United States Patent [19]

Torre

[11] Patent Number: 4,659,990
[45] Date of Patent: Apr. 21, 1987

[54] EDDY CURRENT TEST SYSTEM INCLUDING A MEMBER OF HIGH PERMEABILITY MATERIAL EFFECTIVE TO CONCENTRATE FLUX IN A VERY SMALL REGION OF A PART

[75] Inventor: Rocco Torre, Mt. Clemens, Mich.

[73] Assignee: Magnaflux Corporation, Chicago, Ill.

[21] Appl. No.: 881,491

[22] Filed: Jul. 1, 1986

Related U.S. Application Data

[63] Continuation of Ser. No. 493,420, May 10, 1983, abandoned.

[51] Int. Cl.$^4$ .............................................. G01N 27/82
[52] U.S. Cl. ..................................... 324/238; 324/233
[58] Field of Search ............... 324/217, 218, 225–243, 324/260–262; 336/200, 232

[56] References Cited

U.S. PATENT DOCUMENTS

| | | | |
|---|---|---|---|
| 2,999,977 | 9/1961 | Brown | 336/232 X |
| 3,786,672 | 1/1974 | Gaerttner | 324/243 X |
| 3,840,802 | 10/1974 | Anthony | 324/219 |
| 3,872,379 | 3/1975 | Brooks et al. | 324/242 |
| 4,002,967 | 1/1977 | Fennell | 324/238 |
| 4,075,591 | 2/1978 | Haas | 336/232 X |
| 4,204,159 | 5/1980 | Savian et al. | 324/236 X |
| 4,486,731 | 12/1984 | Westcott | 336/232 |

FOREIGN PATENT DOCUMENTS 2925924  1/1981  Fed. Rep. of Germany ...... 324/240

Primary Examiner—Gerard R. Strecker
Assistant Examiner—Warren S. Edmonds
Attorney, Agent, or Firm—A. J. Brunett; T. W. Buckman

[57] ABSTRACT

An eddy current testing system is disclosed in which a pair of thin one-layer windings are disposed against a pair of thin plates of high permeability magnetic material, about aligned openings in the plates through which a wire is passed, pits and inclusions in the wire being detected by comparing signals corresponding to the electrical impedances on the two windings. The plates of high permeability magnetic material operate to concentrate magnetic flux in small regions of the wire, to obtain a high resolution.

1 Claim, 5 Drawing Figures

U.S. Patent  Apr. 21, 1987  4,659,990
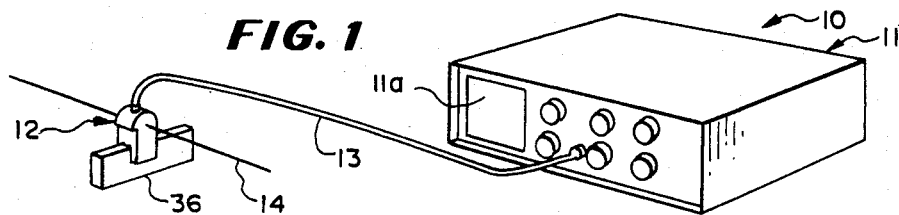
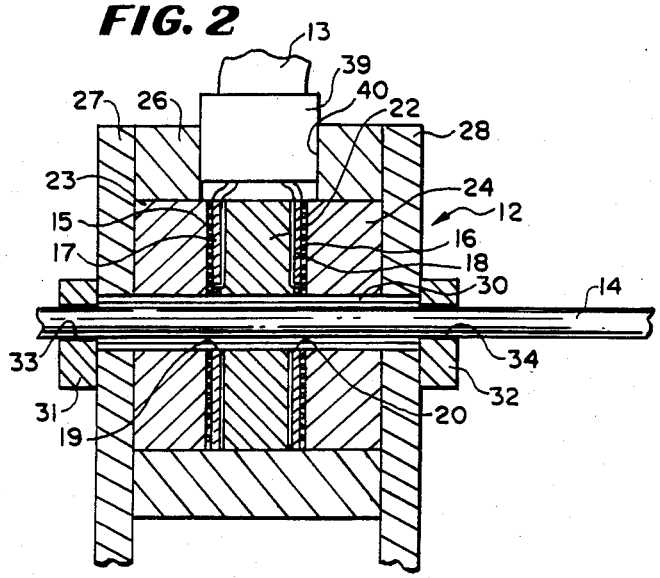
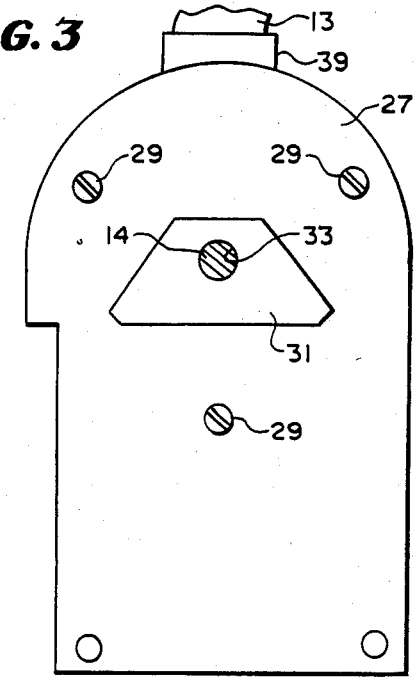
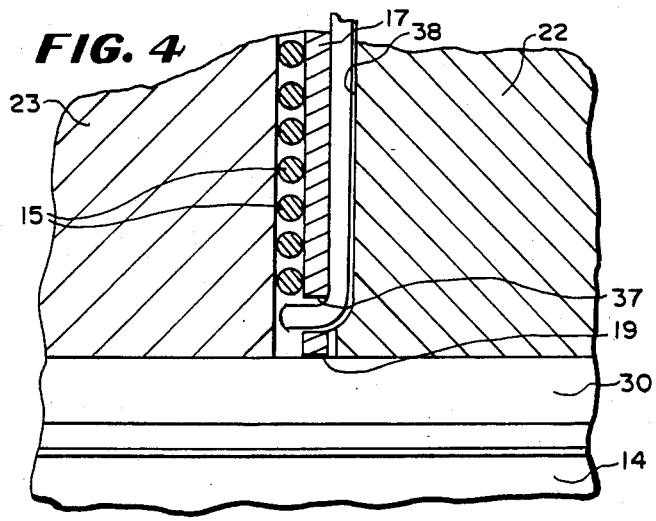
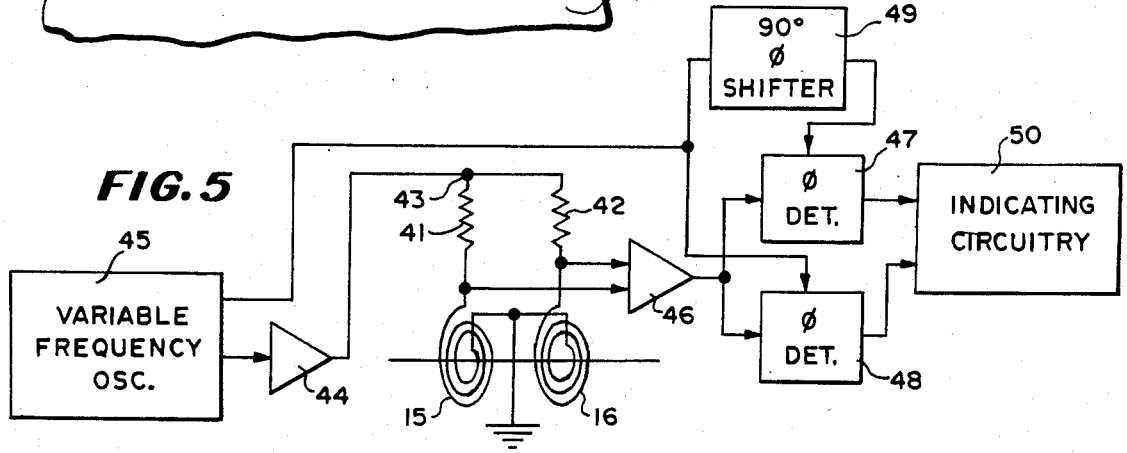

EDDY CURRENT TEST SYSTEM INCLUDING A MEMBER OF HIGH PERMEABILITY MATERIAL EFFECTIVE TO CONCENTRATE FLUX IN A VERY SMALL REGION OF A PART

This application is a continuation of application Ser. No. 493,420 filed May 10, 1983, now abandoned.

This invention relates to an eddy current test system and more particularly to a system for detection of pits, cracks, inclusions and other inhomogeneities in wire or other parts. The system includes a test coil assembly which has a construction such as to obtain high resolution and sensitivity with respect to detection of small inhomogeneities in parts. The assembly is relatively simple in construction, is rugged and reliable and is readily and economically manufacturable while producing highly accurate indications.

BACKGROUND OF THE INVENTION

Eddy current testing systems have heretofore been provided for locating and measuring the severity of surface and near-surface flaws in both magnetic and non-magnetic conductive materials. Such systems have used test coil assemblies in which an output signal is developed corresponding to the difference between signals developed by two windings which are inductive and coupled to two parts or to separate portions of one part. In the testing of elongated parts such as rods, tubes or wires, windings have been provided around longitudinally spaced portions of the part and, as the part is moved through the windings, cracks or other inhomogeneities may be detected from the difference in signals produced by the two windings.

Such eddy current systems have been used extensively and with very satisfactory results in most applications and the possibility of improving the resolution and sensitivity of the systems has not been generally recognized.

SUMMARY OF THE INVENTION

This invention was evolved with the general object of improving the resolution and sensitivity of eddy current testing systems and is based in part upon the discovery that flaws of relatively small size may not be detectable with conventional systems and yet may be such as to form serious defects in a part. In particular, in the manufacture of valve springs for automobile engines, it is found that quite small defects in the wire used for forming the springs may ultimately result in failure of the springs, which can have serious consequences, since the failure of a valve spring can result in irreparable damage to an engine and make it necessary to replace or completely overhaul the engine.

Through experimental work with test coil assemblies, it has been discovered that the resolution and sensitivity may be greatly enhanced by simply providing a member of magnetic material positioned in proximity to a winding to be magnetically linked to the winding, with the member having a terminal end of small area positioned in close proximity to a surface portion of the part. In a test coil assembly for testing of an elongated part, such as wire for use in forming a valve spring, it is found that the member of magnetic material is desirably in the form of a thin plate having an opening therein for passage of the part therethrough, the annular edge of the plate in the opening therein being in close proximity to the outer surface of the part.

It is also found to be desirable that the winding be quite thin, preferably in the form of a single layer against the surface of a plate. It is also found to be desirable that the member be of a high permeability magnetic material.

With these features, it has been found that a very high resolution and sensitivity can be obtained and corrosion pits or the like in the surface of wire have been detected which are of such small size as not to be detected by conventional coil assemblies. It has also been found that inclusions or sub-surface defects can be detected which were not known to exist but which could be such as to cause failure of the valve springs.

Highly advantageous results have been obtained using a "Mu-Metal" magnetic material having a very high permeability. Other magnetic materials may be used, including ferrite materials which are advantageous in minimizing losses when operating at very high frequencies.

Additional features of the invention relate to the construction of the coil assembly, such as to make it physically rugged and highly reliable in operation.

These and other objects, features and advantages of the invention will become more fully apparent from the following detailed description taken in conjunction with the accompanying drawings.

BRIEF DESCRIPTION OF THE DRAWINGS

FIG. 1 is a perspective view illustrating an eddy current system according to the invention, including a test coil assembly for use with wire and an instrument connected to the test coil assembly;

FIG. 2 is an elevational sectional view through the test coil assembly shown in FIG. 1, on an enlarged scale;

FIG. 3 is an end elevational view of the test coil assembly;

FIG. 4 is an enlargement of a portion of the sectional view of FIG. 2, showing the manner in which a winding is formed and supported against a plate of magnetic material; and FIG. 5 is an electrical circuit diagram.

DESCRIPTION OF A PREFERRED EMBODIMENT

Reference numeral 10 generally designates an eddy current system constructed in accordance with the principles of this invention. The system 10 includes an eddy current instrument 11 which is connected to a test coil assembly 12 through a cable 13. The test coil assembly 12 is arranged for passage of a wire 14 longitudinally therethrough, to detect pits, cracks, inclusions or other inhomogeneities therein. The illustrated instrument 11 includes a cathode ray tube having a screen 11a on which defect indications may be produced and the instrument 11 may also operate to energize other forms of indicating means.

The wire 14 may, for example, be wire designed for use in forming valve springs for automobile engines and it is very important that the wire be of the highest possible quality since such valve springs are subjected to repeated high stresses and any slight defect in the spring may result in failure of the spring, and very serious consequences.

FIG. 2 is an elevational sectional view, illustrating the construction of the test coil assembly 12. In the illustrated assembly 12, two windings 15 and 16 are provided which extend spirally about the axis of the wire and in planes which are transverse to the axis of the wire and in longitudinally spaced parallel relation. The electrical impedances of the windings 15 and 16 are affected by the physical characteristics of the portions of the wire adjacent thereto and by comparing the differences in the impedances of the windings, it is possible to detect inhomogeneities in the wire as the wire 14 moves through the test coil assembly 12.

A very important feature of the invention is in the provision of two thin plates 17 and 18 of magnetic material disposed against the coils 15 and 16 to be inductively linked thereto. The plates 17 and 18 are in the form of washers having central openings 19 and 20, the annular edges of the plates 17 and 18 at the openings 19 and 20 being in close proximity to the outer surface of the wire 14 as it passes through the coil assembly 12.

The plates 17 and 18 of magnetic material operate to concentrate magnetic flux in narrow regions of the wire 14 which are in proximity to the edges of the openings 19 and 20 and it is found that a very high sensitivity is obtained with respect to small surface and sub-surface defects in the wire 14. Thus, a high resolution is obtained. Pits and inclusions can be detected which have a very small axial length, much less than the diameter of the wire 14. The arrangement is also advantageous in that the test coil assembly can be very short and it is noted that the plates 17 and 18 also operate to reduce mutual coupling between the windings 15 and 16. The wire 14 can be moved at a relatively high speed and/or the operating frequency may be quite low, without any adverse effects which might otherwise be produced with a short axial distance between windings.

In the illustrated construction, an annular spacer member 22 is provided between the two plates 17 and 18 and a pair of annular members 23 and 24 are provided on the outside, each of the members 22, 23 and 24 being of an insulating material. The members 22, 23 and 24 are disposed within a sleeve 26, also of insulating material, and the assembly thus formed is disposed between a pair of end plates 27 and 28 which are secured together by three bolts 29 in the illustrated construction.

To provide a guide for the wire 14 and to facilitate construction, a tube 30 extends through central openings of the members 22–24 and through central openings in the plates 27 and 28 as well as through the openings 19 and 20 in the plates 17 and 18. In addition, wear shoes or plates 31 and 32 are mounted on the outside, against the outer surfaces of the plates 27 and 28, the two plates 31 and 32 having central openings 33 and 34 which have diameters somewhat less than the inside diameter of the tubing 30. The wear plates 31 and 32 may preferably be of a hardened steel which resists wear.

As shown in the end elevational view of FIG. 3, the end plates 27 are elongated in one direction and have mounting holes for mounting of the coil assembly on a support fixture 36 shown in FIG. 1.

As shown in FIG. 4, the winding 15 is formed as a single layer which is wound spirally on the face of the plate 17. By way of example and not by way of limitation, the winding 15 may be formed from a six foot length of No. 34 wire and it may have approximately forty-seven turns, wound on the plate 17 which has an outer diameter of approximately 32 MM and which has an opening 19 with a diameter of approximately 6.35 MM (0.25 inches). The plate 17 may have a thickness of approximately 0.25 MM (0.01 inches) and may be of a "Mu-Metal". For example, one of the known very high permeability alloys may be used, formed as an alloy of approximately 80% nickel with the balance being either iron alone or iron and other metals. Alloys of less nickel content and other magnetic materials may also be used. For high frequency applications, magnetic materials such as ferrites may be used, having lower permeabilities but producing lower energy losses.

As shown in FIG. 4, an integral lead portion extends from the inner end of the spiral winding 15 and through a notch 37 in the plate 17 and thence radially outwardly along the surface of the plate 17 which may preferably be formed with a radially extending groove, for this purpose. Also, the face of the spacer member 22 may be formed with a facing groove 38. The winding 16 and the plate 18 may preferably have a construction and dimensions substantially identical to those of the windings 15 and 17. Leads from both of the coils 15 and 16 extend to a suitable connector 39 inserted in an opening 40 of the sleeve 26, the cable 13 being connected to the connector 39.

FIG. 5 illustrates the principal components of electrical circuitry of the instrument 11. The coils 15 and 16 are connected in series with a pair of resistors 41 and 42, between a ground connection and a circuit point 43, to form a bridge circuit. The bridge circuit is driven from a bridge amplifier 44, having an output connected to the circuit point 43 and having an input which is supplied with a variable frequency signal from an oscillator 45. Outputs of the bridge circuit, at the junctions between windings 15 and 16 and resistors 41 and 42, are applied to inputs of a differential amplifier 46, the output of which is connected to inputs of a pair of phase detector circuits 47 and 48. The phase detector circuit 47 is connected to the output of a 90° phase shifter 49 which is coupled to the output of the oscillator 45 while the phase detector circuit 48 is coupled directly to the output of the oscillator 45. The phase detector circuits 47 and 48 are thus supplied with reference signals in phase quadrature relation. The outputs of the phase detector circuits 47 and 48 are applied to indicating circuitry 50 which includes circuitry for supplying signals to deflection means of the cathode ray tube, to produce indications on the screen 11a, as shown in FIG. 1. It will be understood that other types of eddy current instrumentation may be used and the indicating circuitry may produce other types of indications.

The use of two windings connected in a bridge configuration is desirable for testing of wire for defects as well as for other types of applications but it will be understood that a single winding may be used and means other than another similar winding may be used for reference purposes. The illustrated construction in which each winding is in the form of a single layer wound spirally and in which each of the plates is quite thin, with a thickness equal to a small fraction of the diameter of the wire 14, is very desirable in attaining a high resolution with respect to detection of pits and inclusions in spring wire or the like. However, other configurations might be used and, for example, a winding may be formed from a plurality of layers or may be randomly wound. A winding may be sandwiched between a pair of members of magnetic material, or may be wound about a member of magnetic material, in certain applications, depending upon the type of part being tested and the type of flaw of principal interest.

It will be understood that modifications and variations may be effected without departing from the spirit and scope of the novel concepts of this invention.

I claim:

1. An eddy current testing system for detection of inhomogeneities in a wire comprising:
    an ac source;
    a test coil assembly energized from said ac source and arranged to be positioned in proximity to said wire to develop an output signal varying as a function of characteristics of a part of said wire which affects the electrical impedence of said test coil assembly, having a first end plate with a central aperture therein, a first annular insulating member adjacent said first end plate on one side thereof, a first flat spiral coil disposed against said first annular insulating member on its side opposite said first end plate, a first washer of magnetic material disposed against said coil on its side opposite said first annular insulating member, a central annular insulating member disposed against said first washer on its side opposite said coil, a second washer of magnetic material disposed against said central insulating member on its side opposite said first washer, a second flat spiral coil disposed against said second washer on its side opposite said central insulating member, a second annular insulating member adjacent said second coil on its side opposite said second washer, a second end plate having a central aperture disposed against said second annular insulating member on its side opposite said second coil, a tube extending through said apertures of said first and second end plates, said insulating members, said washers and said coils, wear shoe means disposed against each of said first and second end plates on their sides opposite said first and second annular insulating members, a sleeve disposed intermediate and connected to said first and second end plates for engaging said coil assembly; and
    means responsive to said output signal to indicate changes in the characteristics caused by inhomogeneties in the wire.

* * * * *